US008581017B2

(12) United States Patent
Holm et al.

(10) Patent No.: US 8,581,017 B2
(45) Date of Patent: Nov. 12, 2013

(54) CONFORMABLE WOUND DRESSING

(75) Inventors: David R. Holm, Hudson, WI (US); Richard L. Jacobson, Stillwater, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 179 days.

(21) Appl. No.: 12/581,275

(22) Filed: Oct. 19, 2009

(65) Prior Publication Data

US 2010/0106121 A1   Apr. 29, 2010

Related U.S. Application Data

(60) Provisional application No. 61/108,296, filed on Oct. 24, 2008.

(51) Int. Cl.
*A61F 13/00* (2006.01)

(52) U.S. Cl.
USPC ............... 602/58; 602/41; 602/42; 602/43

(58) Field of Classification Search
USPC .............. 602/41–59; 128/893, 894, 892; 604/368, 386
See application file for complete search history.

(56) References Cited

U.S. PATENT DOCUMENTS

| 2,148,882 | A | 2/1939 | Scholl |
|---|---|---|---|
| RE24,906 | E | 12/1960 | Ulrich |
| 3,389,827 | A | 6/1968 | Abere et al. |
| 3,529,597 | A | 9/1970 | Fuzak |
| 3,645,835 | A | 2/1972 | Hodgson |
| 3,971,374 | A | 7/1976 | Wagner |
| 4,112,213 | A | 9/1978 | Waldman |
| 4,310,509 | A | 1/1982 | Berglund et al. |
| 4,323,557 | A | 4/1982 | Rosso et al. |
| 4,372,303 | A | 2/1983 | Grossmann et al. |
| 4,472,480 | A | 9/1984 | Olson |
| 4,614,183 | A | 9/1986 | McCracken et al. |
| 4,619,253 | A | 10/1986 | Anhauser et al. |
| 4,732,146 | A | 3/1988 | Fasline et al. |
| 4,737,410 | A | 4/1988 | Kantner |
| 4,738,257 | A | 4/1988 | Meyer et al. |
| 5,088,483 | A | 2/1992 | Heinecke |
| 5,160,315 | A | 11/1992 | Heinecke et al. |

(Continued)

FOREIGN PATENT DOCUMENTS

| EP | 0 303 422 A2 | 2/1989 |
|---|---|---|
| GB | 1 114 893 | 5/1968 |

(Continued)

OTHER PUBLICATIONS

3M Tegasorb™ THIN and 3M Tegasorb Hydrocolloid Dressings; Application and Removal Techniques brochure; 3M Health Care Division; 4 pages; (date unknown but believed to be prior to the date of the filing of the present application).

(Continued)

*Primary Examiner* — Victoria J Hicks (57) ABSTRACT

A wound dressing comprising an absorbent pad, an adhesive layer, and a backing layer is described, along with a dressing support layer configured to retain and deliver the wound dressing to a wound, the dressing support layer having a radial configuration that forms a plurality of alternating covered and uncovered portions of the backing layer along the perimeter of the wound dressing.

15 Claims, 4 Drawing Sheets

(56) References Cited

U.S. PATENT DOCUMENTS

| | | | |
|---|---|---|---|
| 5,429,592 A | 7/1995 | Jensen | |
| 5,501,661 A | 3/1996 | Cartmell et al. | |
| 5,505,958 A | 4/1996 | Bello et al. | |
| 5,531,855 A | 7/1996 | Heinecke et al. | |
| 5,622,711 A | 4/1997 | Chen | |
| 5,633,010 A | 5/1997 | Chen | |
| 5,656,167 A | 8/1997 | Martz | |
| 5,683,354 A | 11/1997 | Levy | |
| 5,704,905 A | 1/1998 | Jensen et al. | |
| 5,738,642 A | 4/1998 | Heinecke et al. | |
| 5,773,022 A | 6/1998 | Nyqvist-Mayer et al. | |
| 5,820,578 A | 10/1998 | Johansen | |
| 5,827,213 A | 10/1998 | Jensen | |
| D408,541 S | 4/1999 | Dunshee et al. | |
| 5,902,260 A | 5/1999 | Gilman et al. | |
| 5,928,972 A | 7/1999 | Mashiko et al. | |
| 5,998,694 A | 12/1999 | Jensen et al. | |
| 6,074,965 A | 6/2000 | Bodenschatz | |
| 6,121,508 A | 9/2000 | Bischof et al. | 602/52 |
| 6,169,224 B1 | 1/2001 | Heinecke et al. | |
| 6,264,976 B1 | 7/2001 | Heinecke et al. | |
| 6,362,387 B1 | 3/2002 | Carlson et al. | |
| 6,495,230 B1 | 12/2002 | Do Canto | 428/41.8 |
| D480,144 S | 9/2003 | Adams et al. | |
| D484,601 S | 12/2003 | Griffiths et al. | |
| D493,230 S | 7/2004 | Liedtke et al. | |
| 6,838,589 B2 * | 1/2005 | Liedtke et al. | 602/58 |
| D503,982 S | 4/2005 | Liedtke et al. | |
| 6,881,875 B2 | 4/2005 | Swenson | |
| 6,927,315 B1 | 8/2005 | Heinecke et al. | |
| D511,005 S | 10/2005 | Liedtke et al. | |
| D516,729 S | 3/2006 | Liedtke et al. | |
| 7,030,288 B2 | 4/2006 | Liedtke et al. | |
| 7,091,394 B2 | 8/2006 | Kolte et al. | |
| 7,304,202 B2 * | 12/2007 | Sigurjonsson et al. | 602/58 |
| 7,518,031 B2 | 4/2009 | Liedtke et al. | |
| 2003/0088202 A1 | 5/2003 | Gilman | |
| 2004/0049146 A1 | 3/2004 | Kolte et al. | |
| 2005/0113733 A1 | 5/2005 | Liedtke et al. | |
| 2006/0061791 A1 | 3/2006 | Laaspere et al. | |
| 2006/0142687 A1 | 6/2006 | Liedtke et al. | |
| 2007/0156075 A1 | 7/2007 | Heinecke | |
| 2007/0282238 A1 * | 12/2007 | Madsen et al. | 602/48 |
| 2008/0019310 A1 | 1/2008 | Sebire et al. | |
| 2008/0039759 A1 | 2/2008 | Holm et al. | |
| 2008/0051687 A1 | 2/2008 | Rogers | |
| 2008/0281246 A1 | 11/2008 | Effing et al. | |
| 2009/0177136 A1 | 7/2009 | Liedtke et al. | |
| 2010/0106120 A1 | 4/2010 | Holm | |

FOREIGN PATENT DOCUMENTS

| | | |
|---|---|---|
| GB | 1 251 203 | 10/1971 |
| GB | 2 131 299 | 6/1984 |
| JP | 2-61933 | 5/1990 |
| JP | 8-103462 | 4/1996 |
| JP | 2003-102774 | 4/2003 |
| JP | 2004-513704 | 5/2004 |
| WO | WO 88/08787 | 11/1988 |
| WO | WO 97/07760 | 3/1997 |
| WO | WO 99/27975 | 6/1999 |
| WO | WO 99/28539 | 6/1999 |
| WO | WO 2004/073567 | 9/2004 |

OTHER PUBLICATIONS

3M Tegasorb™ Hydrocolloid Dressing 3M Tegasorb™ Thin Hydrocolloid Dressing; Product Profile brochure; 3M Health Care Division; 17 pages; (date unknown but believed to be prior to the date of the filing of the present application).

International Search Report; PCT/US2009/061150; Jan. 13, 2010; 3 pages.

Written Opinion of the International Searching Authority; PCT/US2009/061150; Jan. 13, 2010; 4 pages.

International Search Report; PCT/US2007/075169, Nov. 7, 2007, 4 pages.

Written Opinion of the International Searching Authority; PCT/US2007/075169, Nov. 7, 7 pages.

International Search Report; PCT/US2009/061791, Jan. 5, 2010, 3 pages.

Written Opinion of the International Searching Authority; PCT/US2009/061791, Jan. 5, 2010, 7 pages.

Written Opinion of the International Searching Authority; PCT/US2004/03688 Jun. 9, 2004, 4 Pages.

International Search Report, PCT/US2004/03688, Jun. 9, 2004, 1 Page.

* cited by examiner

CONFORMABLE WOUND DRESSING

CROSS-REFERENCE TO RELATED APPLICATION

This application claims priority to U.S. Provisional Patent Application No. 61/108,296, filed Oct. 24, 2008, the disclosure of which is incorporated by reference herein in its entirety.

FIELD OF THE INVENTION

This disclosure relates to wound dressings, and more particularly to a thin film composite dressing and a support delivery system.

BACKGROUND OF THE INVENTION

Wound dressings using an absorbent central area surrounded by a larger adhesive film are known. For example, U.S. Pat. No. 5,738,642 (the '642 patent) shows a wound dressing and delivery system comprising a thick absorbent pad placed in the center of a thin backing A carrier frame surrounds the perimeter of the wound dressing, providing support (e.g. rigidity) to the backing to facilitate handling of the dressing during application to a wound. Such dressings are often applied to relatively flat areas of the body, such as the chest or abdomen. When these dressings are applied to irregularly shaped parts of the body, such as the shoulder, the dressings are sometimes cut toward their center to make a cone shaped dressing, but these dressings have significant limitations, including the risk of infection along the line of the cut line, difficulty in applying with one hand, and leakage of fluids from the wound along the cut line.

SUMMARY OF THE INVENTION

The present disclosure provides a wound dressing having a thin, flexible adhesive film surrounding a thick absorbent pad, and delivery system that facilitates the handling and application of the wound dressing. The wound dressing is readily handled and applied with one hand, which frees up the other hand to help position the patient or parts of the patient to ensure better application of the wound dressing. In further embodiments, the wound dressing is configured to be applied with two hands, particularly for placement in hard to reach areas of the body.

The wound dressing is constructed so as to have improved adhesion to irregularly shaped surfaces, such as the inner crease of the elbow, and to permit easy application to the irregularly shaped surfaces. The wound dressing and delivery system are well suited to positioning an absorbent pad onto a concave or convex surface. For example, the wound dressing and delivery system are suitable for applying an absorbent pad to the inner crease of the elbow or the sacrum-coccyx notch area, while maintaining an intact sterile perimeter around the wound dressing.

In certain embodiments, the wound dressing and delivery system include a wound dressing comprising an adhesive layer on a backing layer. Optionally, an absorbent pad or other material is applied or attached to the adhesive layer. A dressing support layer is positioned on top of the backing layer, and is configured to retain and deliver the wound dressing to a wound. In particular, the dressing support layer has a radial configuration of extensions that support the backing layer along the perimeter of the wound dressing, while also allowing the dressing to be easily applied to convex surfaces and other non-planer surfaces. The dressing support layer further comprises at least one tab that extends beyond the edge of the baking layer of the wound dressing wherein the tab includes an area of weakness which provides additional structure and rigidity to the wound dressing when the tab is held and manipulated by the user.

These and various other advantages and features characterizing the invention are pointed out with particularity in the claims annexed hereto and forming a part hereof. However, for a better understanding of the invention, its advantages, and objects obtained by its use, reference should be made to the accompanying drawings and descriptive matter, in which embodiments of the invention are illustrated and described.

BRIEF DESCRIPTION OF THE DRAWINGS

The invention will be further described with reference to the drawings, wherein corresponding reference characters indicate corresponding parts throughout the several views, and wherein.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION

The present disclosure is directed to a wound dressing and delivery system, as well as to methods of positioning and applying the wound dressing to a patient, especially with one hand. The wound dressing and delivery system are particularly suited for application over a concave surface of a patient, such as the inner crease of the elbow, or a convex surface, such as a shoulder. The wound dressing permits a highly absorbent material to be placed against the wound, while the delivery system aids in positioning the wound dressing on the body and forming a seal around the area surrounding the wound.

In some embodiments, the wound dressing comprises an absorbent pad, a backing layer, and an adhesive layer on the backing layer facing the absorbent pad. The adhesive layer and backing layer form a perimeter around the absorbent pad and hold the absorbent pad in place on a wound. The perimeter formed by the adhesive layer and backing layer keeps the absorbent pad properly positioned, and also helps maintain a sterile environment around the wound. The adhesive layer and backing layer are typically extremely thin, and generally very flexible. If the adhesive layer and backing layer are not properly supported during application, they can easily fold over and adhere to themselves, preventing proper application over a wound.

The delivery system described herein provides an easy and effective way to position and apply the wound dressing to a patient while effectively supporting the perimeter of the dressing to prevent excessive undesirable folding, while allowing controlled, limited folding of the backing layer sufficient to properly contact the patient's uneven skin surface.

Figure 1:
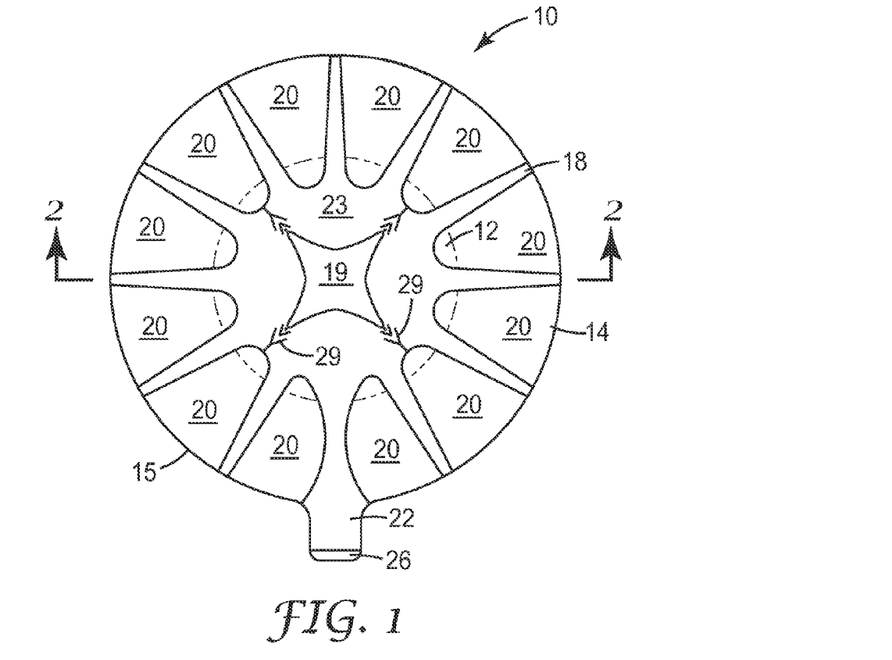
FIG. 1 is a top perspective view of a prior art wound dressing.
Figure 2:
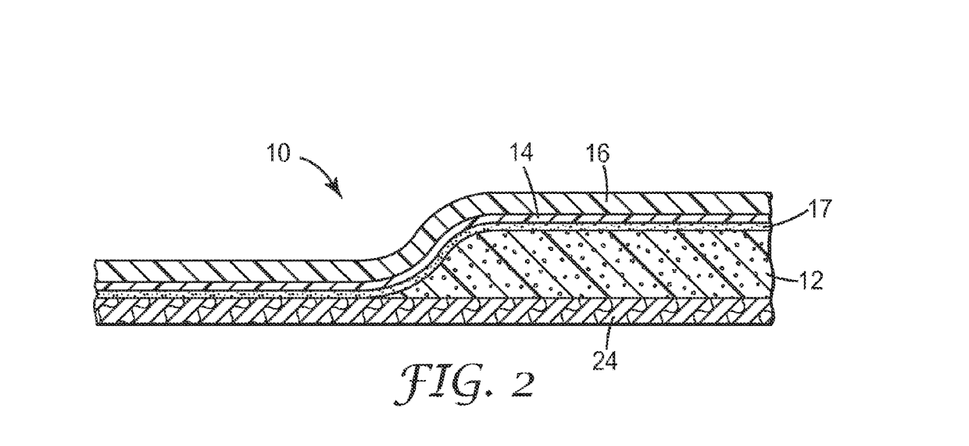
FIG. 2 is an enlarged cross section of the dressing of FIG. 1 taken along lines 2-2.

Turning now to the figures, FIGS. 1 and 2 show an example of a known wound dressing and delivery system. FIG. 1 shows a perspective view, and FIG. 2 shows an enlarged cross-sectional view of the wound dressing of FIG. 1 taken along lines 2-2. The wound dressing 10 includes a centrally located absorbent pad 12. The absorbent pad 12 is covered by an adhesive layer 17 on a backing layer 14 that extends out to the perimeter 15 of the wound dressing 10. The backing layer 14 is typically extremely thin, flexible, and either transparent or translucent, allowing the absorbent pad 12 to be viewed through it. The delivery system is particularly useful in connection with a wound dressing 10 having a relatively heavy or stiff absorbent pad 12 positioned on a highly conformable backing layer 14 that is light and flexible relative to the pad 12.

At least one dressing support layer 16 is positioned over the wound dressing 10. The dressing support layer 16 has a substantially radial configuration, with a plurality of extensions 18 radiating generally from the center 19 of the dressing 10. The support layer 16 forms a plurality of alternating uncovered portions 20 of the adhesive backing layer 14, separated from one another by the extensions 18 along the adhesive perimeter 15 of the wound dressing. The support layer 16 can be a single piece of material, such as a polymeric film, or can be two or more distinct pieces. The support layer 16 shown in FIGS. 1 and 2 are provided with paths 29 which provide a controlled tear of the dressing support layer 16, typically after application of the wound dressing 10.

In most implementations, the support layer 16 comprises a plurality of extensions 18 radiating from the interior of the dressing 10 toward its edges. The radial configuration of the dressing support layer 16 allows the perimeter 15 of the dressing 10 to be pressed around a convex surface. During application, the uncovered portions 20 of the backing layer 14 between the extensions 18 can contract to maintain a good seal around the edges of the wound. This contraction is typically localized so that individual portions 20 will contract and even fold upon themselves. However, folds or contact between the portions 20 is minimized. In this manner, the wound dressing 10 can have a relatively even, smooth edge without major flaps of the backing layer 14 folded over onto itself.

As can be seen in FIGS. 1 and 2, the dressing support layer 16 may comprise at least one portion that extends beyond the edge of the backing layer 14 of the wound dressing 10 to form a tab 22. The tab 22 can be held during positioning of the wound dressing 10.

In addition, the wound dressing 10 typically includes a carrier film 24, also having a tab 26. The carrier film 24 covers the surface of the wound dressing applied to the patient, generally making contact with the absorbent pad 12 and the periphery of the adhesive layer 17. The carrier film 24 remains attached to wound dressing 10 until a user is ready to apply the dressing. The carrier film 24 may be a single piece or multiple piece release liner, and may be part of or laminated to the package (not shown) containing the dressing, or merely enclosed along with the dressing within the package. The carrier film 24 keeps the adhesive clean during storage and shipping of the wound dressing 10.

As shown in FIGS. 1 and 2, the extensions 18 converge on the center 19 of the wound dressing 10 but typically do not cover the center 19. In general, the perimeter of the dressing support layer 16 is releasably adhered to the backing layer 14, but at least part of the center portion 19 of the dressing support layer 16 is not adhered to the backing layer 14. This results in the formation of a plurality of centrally located tabs 23 configured for removing the dressing support layer from the backing layer after the dressing 10 has been applied to a patient. In some embodiments, at least part of the center of the dressing support layer 16 is prevented from adhering to the backing layer 14 by means of a liner (not shown) on the side of dressing support layer 16 facing backing layer 14. This liner also aids in removal of the support layer, and in some embodiments assists in elevating the tabs 23 when the dressing 10 is applied to a wound.

In reference now to FIG. 2, an enlarged cross section of a wound dressing 10, taken along lines 2-2 of FIG. 1 is shown. This cross section shows a thin, flexible backing layer 14, which in is partially covered by support layer 16 on one major surface, and an adhesive layer 17 and absorbent pad 12 on the other. As described above, a carrier film, or release liner 24, may be disposed on the wound dressing 10 for protecting the absorbent pad 12 and surrounding adhesive layer 17.

The wound dressing 10 is typically applied to a patient by first cleaning the wound and making sure the area around the wound is ready to receive a dressing. The carrier film 24 is then removed from the dressing, for example, by grasping tab 26 and peeling away the carrier film 24, exposing the bottom of the absorbent pad 12 and the perimeter of the adhesive layer 17 on the backing layer 14. As the wound dressing 10 is held by one or more of the tabs 22 extending from the dressing support layer 16, the center of the absorbent pad 12 is brought in contact with the wound, and then the edges of the dressing 10 are gently and smoothly pressed against the patient, thereby bringing the exposed adhesive perimeter of the backing layer 14 in contact with the patient. Generally the areas 20 of the backing layer 14 intermediate the extensions 18 contract to conform around the skin surface. When applied to convex surfaces, the contractions can cause the tabs 23 to rise off the surface of the backing layer 14. After the dressing 10 is properly in position and adhered to a patient's skin, the support layer 16 can be removed. Generally removal of support layer 16 is accomplished by grasping tabs 23 and then using a peeling motion toward the edges of the dressing 10 to remove the support layer 16.

Figure 3:
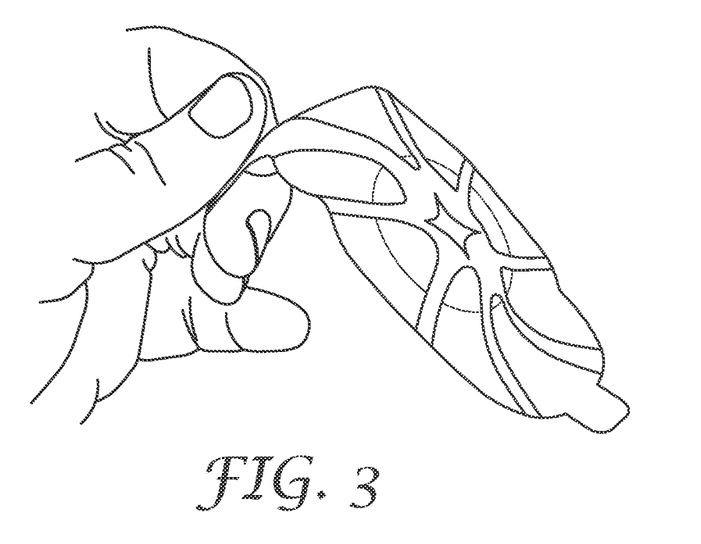
FIG. 3 is a perspective view of the wound dressing of FIG. 1, being held by tab 22.

The wound dressing 10 of FIGS. 1 & 2, while useful in many applications, presents challenges in others. In some applications, after removing the carrier film 24, a user may wish to apply the wound dressing 10 to a patient with one hand, for example, when applying a wound dressing to the sacrum-coccyx notch area. As can be seen in FIG. 3, when the wound dressing of FIG. 1 is held with one hand by a tab 22, the dressing lacks sufficient rigidity to be held in a substantially horizontal position to facilitate application to a patient. As such, it would be difficult to apply the dressing 10 to a patient with one hand when holding the dressing in this horizontal position.

Figure 4:
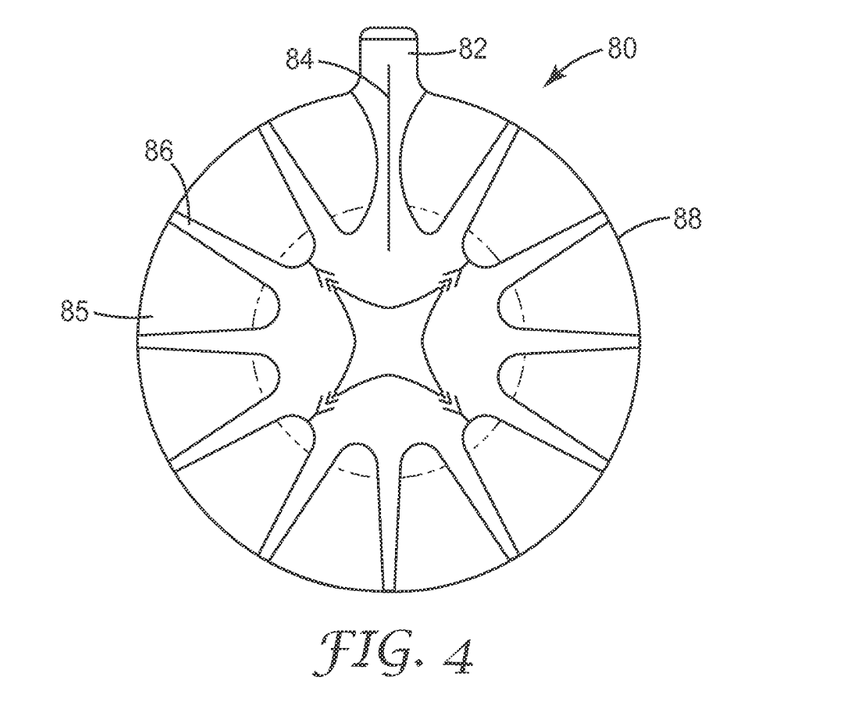
FIG. 4 is a perspective view of a wound dressing according to an embodiment of the present disclosure.

Turning now to FIG. 4, a wound dressing 80 in accordance with the present disclosure is shown. The wound dressing 80 as shown in FIG. 4, is generally similar in structure to the wound dressing 10 of FIG. 1 and has a support layer 86 comprising a single tab 82, extending beyond the edge 88 of the backing layer 85 of the wound dressing 80. To provide further rigidity when the dressing 80 is held by tab 82, an area of weakness 84, in the form of a crease, a series of perforations, a slit, or the like, is provided along a radial line of the support layer 86 extending generally from the center of the dressing 80, toward, and in some embodiments, through, the tab 82.

Figure 5:
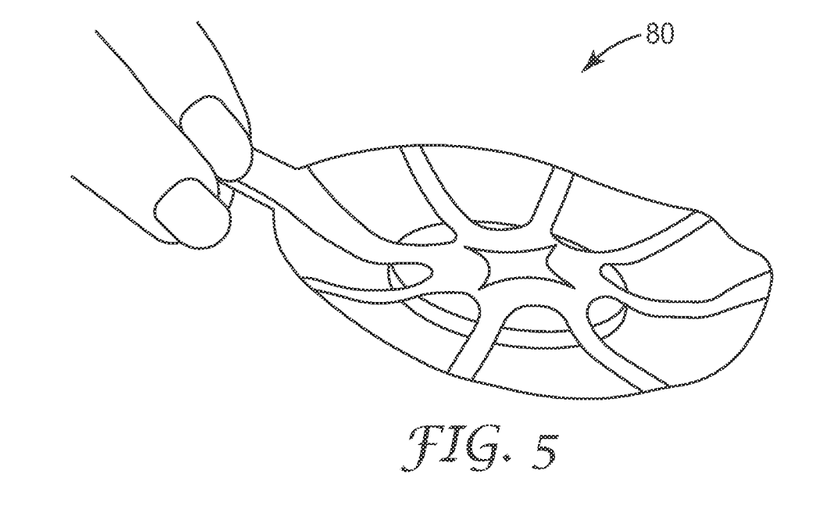
FIG. 5 is a perspective view of the wound dressing of FIG. 4, being held by tab 82.

When a user grasps the dressing 80 from the tab 82, the area of weakness 84, facilitates the edges of the support layer 86 along the area of weakness 84 to fold toward one another, creating a "V" like structure which creates additional stiffness and structure to the support layer. As illustrated in FIG. 5, the additional support provided by the area of weakness 84 in the support layer 86 enables the dressing 80 to be held in a substantially horizontal position with one hand. In this way, the dressing 80 may be more easily applied to a portion of the body that is concave in nature (e.g., in between toes, on the inside of an elbow, or in the sacrum-coccyx notch area) because the other hand is free to position the patient's body as necessary to more readily apply the dressing.

As may be appreciated by one skilled in the art, the embodiment shown in FIGS. 4 & 5 may be configured with two or more tabs coupled with a corresponding area of weakness. Further, the area of weakness may be positioned anywhere along a radial line of the support layer 86 leading to the one or more tab(s) 82, and may be of varying length. In an embodiment, the dressing 80 has a length (including the tab) of approximately 100 cm, and the area of weakness 84 has a length of approximately 25 cm, and is positioned parallel to the portion of the support layer 86 that is associated with the tab 82. In an embodiment, the area of weakness 84 takes the form of a fold, linear slit, a sinusoidal wave slit, or a series of perforations in the shape of dots, holes, V-shaped cuts, or Y-shaped cuts in the support layer 86 of the dressing. As one skilled in the art may appreciate, the area of weakness may take on several forms without departing from the spirit of the invention.

In an embodiment, the area of weakness extends at least 20% of the length of the support layer associated with the tab, and in a further embodiment, at least 40%. In one embodiment, the area of weakness extends from the area proximate the edge of an absorbent pad on the dressing to a portion of the tab that is proximate the edge of the backing layer. In a further embodiment, the area of weakness extends from an area over the edge of the absorbent pad to an area of the tab that is free of the backing layer.

Figure 6:
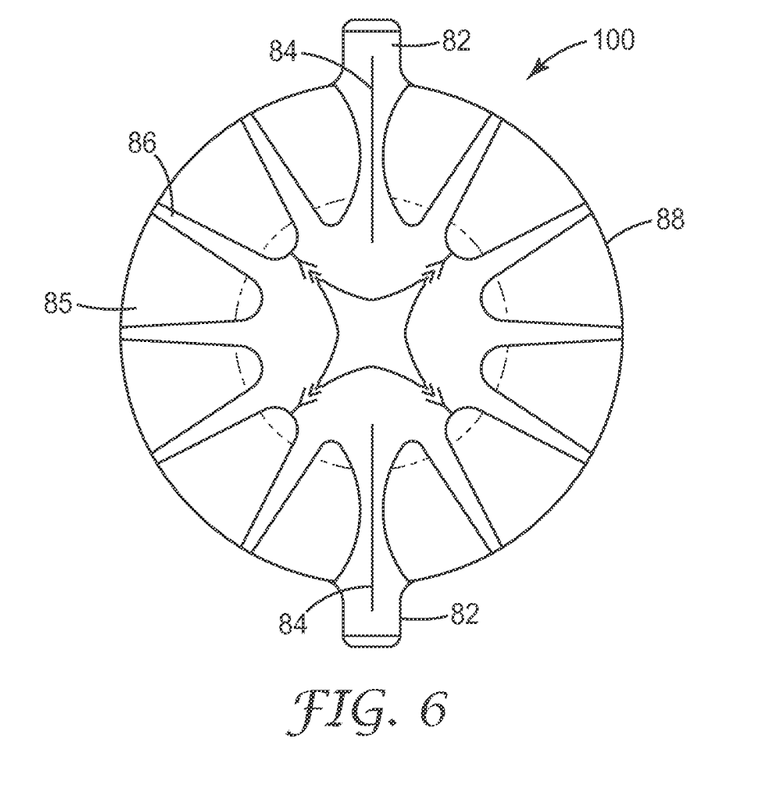
FIG. 6 is a perspective view of an alternative embodiment of a wound dressing.

FIG. 6 shows a wound dressing 100 in accordance with a further embodiment of the disclosure, the wound dressing having a generally similar structure as the dressing shown in FIG. 4, and having two tabs 102, with corresponding slits 104 for assisting the user in handling the dressing 100. The dressing 100 of FIG. 6 has a support layer 86, for supporting a backing layer 85, wherein the support layer also forms a radial configuration.

The dressing 100 depicted in FIG. 6 is well suited for placement with two hands to an area of the body having a narrow crease such as in between the toes or fingers.

Figure 7:
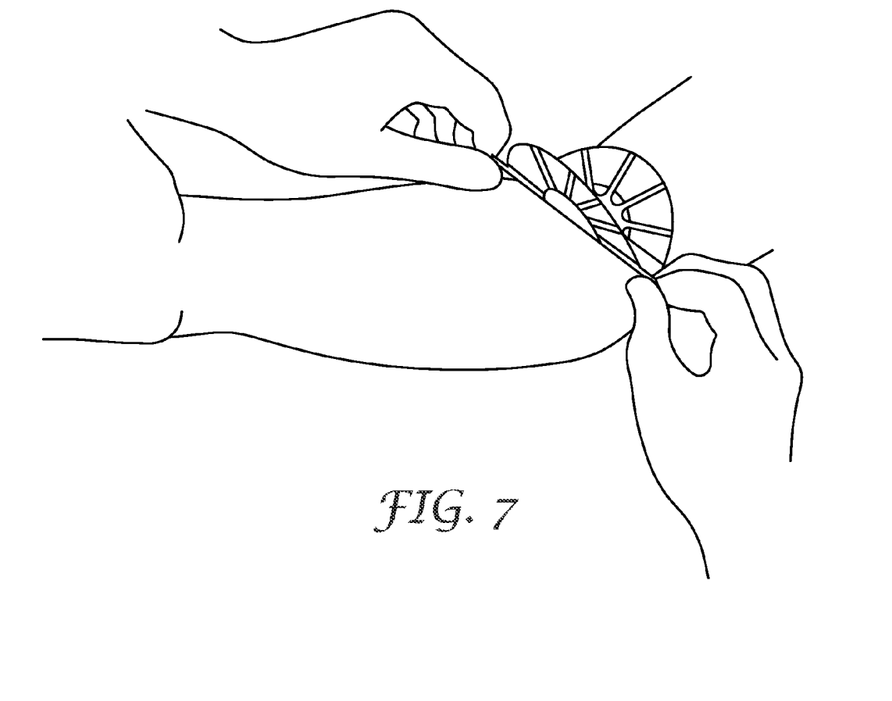
FIG. 7 is a perspective view of the wound dressing of FIG. 6 being applied to a patient.

To apply the dressing 100 to a patient, a user would first remove the release liner, if present, and then grasp the dressing 100 by tabs 82, while bending the dressing such that outer edges 88 of the dressing are moved toward one another such that the dressing forms a cup-like shape. As illustrated in FIG. 7, this enables the user to more easily place the dressing in a creased area of the body such as in side the elbow, or in between the fingers or toes.

As one skilled in the art would appreciate, other implementations are appropriate in order to add or take away from the aspects the various embodiments of the wound dressings as described herein. For example, the backing layer 14 can be multiple films or coatings without diverging from the invention or deviating from the meaning of the term "film" as used herein. Similarly, the absorbent pad 12 can include multiple sub-layers, including films, webs, sheets, etc. Also, additional layers and films of other materials can be added between the materials described herein without deviating from the invention.

The number of exposed areas 20 of backing layer 14 along the perimeter 15 of the wound dressing 10 can vary in number, shape, and size. However, typically there are at least two, generally at least four distinct exposed areas, and more commonly eight or more distinct areas. In some implementations less than 80 percent of the periphery (that portion outside of the absorbent) of the backing layer 14 is covered by the support layer 16, while in other implementations less than 60 percent of the periphery of the backing layer 14 is covered by the support layer 16, while in yet other implementations less than 40 percent of the periphery of the backing layer 14 is covered by the support layer 16.

In some embodiments, paths 29 in the support layer 16 provide controlled tear of the dressing support layer 16 when tabs 23 are lifted to remove the dressing support layer 16 during and/or after application of the dressing 10 to a patient. However, alternative configurations are possible including but not limited to linear, angled, Y-shaped, dual-angled offset, circular holes, and alternating combinations thereof. In FIG. 1, path 29 is shown with a plurality of perforations in an arrow configuration.

Pressure sensitive adhesive layer 17 is generally provided on one major surface of the backing layer 14 in order to make it adhesive, and a low adhesion coating (low adhesion backsize or LAB) is provided on the other major surface of the backing layer 14 on the side that comes in contact with the support layer 16. The low adhesion coating reduces the need to change the dressing 10 due to unwanted dressing removal when other tapes or devices are placed on the dressing 10 and removed, and reduces the surface friction of the dressing 10 on linen or other fabrics, thereby offering additional protection against the accidental removal of dressing 10. A description of a low adhesion backing material suitable for use with the present invention can be found in U.S. Pat. Nos. 5,531,855 and 6,264,976, which are compatible with a heat seal bond described below, and are incorporated herein in their entirety.

When the support layer 16 is removed from the backing layer 14, the force applied to the edge of the backing layer 14 is generally perpendicular to the perimeter of the dressing 10. This force contrasts with peel forces of conventional support layers, which are parallel to the perimeter of the wound dressing, and which often lift the perimeter off the surface of the patient, potentially loosening the dressing or creating a path for leakage of fluids from the wound.

The absorbent pad 12 of dressing 10 is sometimes referred to as an "island pad" because the backing layer 14 extends substantially beyond the absorbent pad 12, typically beyond the entire periphery of the absorbent pad 12. For example, the length and width of the absorbent pad can be 6 cm by 6 cm, while a backing for this pad can be 9 cm by 9 cm. The pressure sensitive adhesive layer 17 on the peripheral portion of the backing layer 14 is thus not supported or reinforced by the relatively heavy and stiff absorbent pad 12, and absent the benefits of dressing support layer 16 would be difficult to handle without folding, wrinkling or otherwise adhering to itself, rather than adhering to the skin, before and during application.

The support layer 16 is preferably attached to the second major surface of the backing layer 14 (over the low adhesion backing). The bond between the support layer 16 and the backing layer 14 is stronger than the bond between the pressure sensitive adhesive 17 and the carrier layer 24 so that the backing layer 14 remains attached to the support layer 16 when the carrier layer 24 is removed from the dressing 10. Once the carrier layer 24 and dressing 10 are separated, only the support layer 16 and absorbent pad 12 provide significant rigidity to the backing layer 14.

The absorbent pad 12 can comprise a hydrocolloid and hydrogel pad having a thickness of at least 1 mm (e.g., most preferably 3-9 mm), and the backing layer 14 can comprise a transparent elastic polymeric film (e.g., urethane) having a thickness no greater than 0.1 mm (e.g., most preferably 0.021-0.051 mm). It will be appreciated that in this embodiment the absorbent pad 12 is much thicker, stiffer and heavier than the backing layer 14.

Additional aspects of various components of the invention will now be described in greater detail.

Absorbent Pad

Absorbent pad 12 can be manufactured of any of a variety of materials including, but not limited to, woven or nonwoven cotton or rayon. Absorbent pad 12 is useful for containing a number of substances, optionally including antimicrobial agents, drugs for transdermal drug delivery, chemical indicators to monitor hormones or other substances in a patient, etc.

The absorbent may include a hydrocolloid composition, including the hydrocolloid compositions described in U.S. Pat. Nos. 5,622,711 and 5,633,010, the disclosures of which are hereby incorporated by reference. The hydrocolloid absorbent may comprise, for example, a natural hydrocolloid, such as pectin, gelatin, or carboxymethylcellulose (CMC) (Aqualon Corp., Wilmington, Del.), a semi-synthetic hydrocolloid, such as cross-linked carboxymethylcellulose (X4ink CMC) (e.g. Ac-Di-Sol; FMC Corp., Philadelphia, Pa.), a synthetic hydrocolloid, such as cross-linked polyacrylic acid (PAA) (e.g., CARBOPOL™ No. 974P; B.F. Goodrich, Brecksville, Ohio), or a combination thereof. Generally, the hydrocolloid absorbent component comprises from about 5 percent to about 60 percent by weight of the absorbent composition. When preparing an absorbent composition for use in a wound dressing the hydrocolloid absorbent preferably comprises from about 20 percent to about 40 percent by weight of the composition. Absorbent materials may also chosen from other synthetic and natural materials including polymer gels and foams.

Backing Materials

Suitable backing materials for backing layer 14 include, for example, nonwoven fibrous webs, woven fibrous webs, knits, films and other familiar backing materials. The backing materials are typically translucent or transparent polymeric elastic films. The backing can be a high moisture vapor permeable film backing U.S. Pat. No. 3,645,835, the disclosure of which is hereby incorporated by reference, describes methods of making such films and methods for testing their permeability. A combination of the aforementioned backings could also be used.

The backing advantageously should transmit moisture vapor at a rate equal to or greater than human skin. In some embodiments, the adhesive coated backing layer transmits moisture vapor at a rate of at least 300 g/m$^2$/24 hrs/37° C./100-10% RH, frequently at least 700 g/m$^2$/24 hrs/37° C./100-10% RH, and most typically at least 2000 g/m$^2$/24 hrs/37° C./100-10% RH using the inverted cup method.

The backing layer 14 is generally conformable to anatomical surfaces. As such, when the backing layer 14 is applied to an anatomical surface, it conforms to the surface even when the surface is moved. The backing layer 14 is also conformable to animal anatomical joints. When the joint is flexed and then returned to its unflexed position, the backing layer 14 can be made such that it stretches to accommodate the flexion of the joint, but is resilient enough to continue to conform to the joint when the joint is returned to its unflexed condition.

A description of this characteristic of backing layers 14 for use with the present invention can be found in issued U.S. Pat. Nos. 5,088,483 and 5,160,315, the disclosures of which are hereby incorporated by reference in their entirety. Specific suitable backing materials are elastomeric polyurethane, copolyester, or polyether block amide films. These films combine the desirable properties of resiliency, high moisture vapor permeability, and transparency found in backings.

Support Layer

The material used to form the support layer 16 is generally substantially more rigid than the backing layer 14 to prevent the backing layer 14 from improperly wrinkling during application to a patient. The support layer 16 can be heat-sealable to the backing layer 14 with or without a low adhesion coating described above. In general, the support layer materials can include, but are not limited to, polyethylene/vinyl acetate copolymer-coated papers and polyester films. One example of a suitable support layer material is a polyethylene/vinyl acetate copolymer coated super calendared Kraft paper (1-80BKG-157 PE; Loparex of Willowbrook, Ill.).

The support layer 16 can include perforations to aid in separating portions of the support layer 16 after application of the dressing 10 in a patient. Spacing and shape of the perforations are adjusted to give a support layer with relatively easy to tear performance on removal of the support layer from the applied dressing. The perforations may be shaped in accordance with any of the accepted perforation patterns including linear, angled, Y-shaped, V-shaped, dual-angled offset, sinusoidal, etc.

Pressure Sensitive Adhesive

Various pressure sensitive adhesives can be used to form adhesive layer 17 on the backing layer 14 to make it adhesive. The pressure sensitive adhesive is usually reasonably skin compatible and "hypoallergenic", such as the acrylate copolymers described in U.S. Pat. No. RE 24,906, the disclosure of which is hereby incorporated by reference. Particularly useful is a 97:3 iso-octyl acrylate:acrylamide copolymer, as is 70:15:15 isooctyl acrylate:ethyleneoxide acrylate:acrylic acid terpolymer described in U.S. Pat. No. 4,737,410, the disclosure of which is hereby incorporated by reference is suitable. Additional useful adhesives are described in U.S. Pat. Nos. 3,389,827, 4,112,213, 4,310,509, and 4,323,557, the disclosures of which are hereby incorporated by reference. Inclusion of medicaments or antimicrobial agents in the adhesive is also contemplated, as described in U.S. Pat. Nos. 4,310,509 and 4,323,557, both of which are also hereby incorporated by reference.

Carrier Films

Carrier films 24 suitable for use with the invention can be made of kraft papers, polyethylene, polypropylene, polyester or composites of any of these materials. The films are preferably coated with release agents such as fluorochemicals or silicones. For example, U.S. Pat. No. 4,472,480, the disclosure of which is hereby incorporated by reference, describes low surface energy perfluorochemical liners. The liners are papers, polyolefin films, or polyester films coated with silicone release materials. Examples of commercially available silicone coated release papers are POLYSLIK™, silicone release papers available from Rexam Release (Bedford Park, Ill.) and silicone release papers supplied by Loparex Inc. (Willowbrook, Ill.).

As various changes could be made in the above constructions, compositions and methods without departing from the scope of the invention as defined in the claims, it is intended that all matter contained in the above description or shown in the accompanying drawings be interpreted as illustrative and not in a limiting sense.

What is claimed is:

1. A wound dressing and delivery system comprising:
   a wound dressing comprising a backing layer having a first major surface and a second major surface;
   an adhesive layer on at least a portion of the first major surface of the backing layer; and
   a dressing support layer releasably adhered to the second major surface of the backing layer, the dressing support layer having a radial configuration that forms a plurality of alternating covered and uncovered portions of the backing layer along the perimeter of the wound dressing, wherein the dressing support layer further comprises at least one tab that extends beyond the edge of the backing layer of the wound dressing, wherein the at least one tab includes an area of weakness that extends along a radial line of the dressing support layer from a region of the dressing support layer that overlaps the backing layer to an area of the at least one tab that is free of the backing layer.

2. The wound dressing and delivery system of claim 1, wherein the wound dressing further comprises an absorbent material disposed on at least a portion of the first major surface of the backing layer.

3. The wound dressing of claim 2, wherein the area of weakness extends from a location on the dressing support layer over the absorbent material to a location beyond the periphery of the backing layer.

4. The wound dressing and delivery system of claim 1 or 2, further comprising a release liner in contact with the backing layer of the wound dressing, wherein the backing layer is intermediate the release liner and the dressing support layer.

5. The wound dressing and delivery system of claim 2, wherein the absorbent material is selected from the group consisting of hydrogel, a hydrocolloid, a foam, a swelling synthetic polymer, a synthetic nonwoven material, and a natural nonwoven material.

6. The wound dressing and delivery system of claim 2, comprising two or more layers of the absorbent material.

7. The wound dressing and delivery system of claim 1, wherein the area of weakness is taken from the group consisting of: a series of perforations, and a slit.

8. The wound dressing of claim 1, wherein the length of the area of weakness is at least 20% of the length of an extension of the dressing support layer that contains the area of weakness.

9. The wound dressing of claim 1, wherein the length of the area of weakness is at least 40% of the length of an extension of the dressing support layer that contains the area of weakness.

10. The wound dressing and delivery system of claim 1, wherein the dressing support layer covers less than 80 percent of the second major surface of the backing layer.

11. The wound dressing and delivery system of claim 1, wherein the dressing support layer covers less than 60 percent of the second major surface of the backing layer.

12. The wound dressing and delivery system of claim 1, wherein the backing layer of the wound dressing comprises a transparent or translucent polymeric film.

13. A method of applying a wound dressing to a wound, comprising:
   (a) providing a wound dressing and delivery system, comprising:
      (i) a wound dressing comprising a backing layer having a first major surface and a second major surface;
      (ii) an adhesive layer on at least a portion of the first major surface of the backing layer; and
      (iii) a dressing support layer releasably adhered to the second major surface of the backing layer, the dressing support layer having a radial configuration that forms a plurality of alternating covered and uncovered portions of the backing layer along the perimeter of the wound dressing, wherein the dressing support layer further comprises at least one tab that extends beyond the edge of the backing layer of the wound dressing, wherein the at least one tab includes an area of weakness that extends along a radial line of the dressing support layer from a region of the dressing support layer that overlaps the backing layer to an area of the at least one tab that is free of the backing layer;
   (b) manipulating the at least one tab to form a V-shape associated with the at least one tab;
   (c) positioning the wound dressing over the wound; and
   (d) applying a surface pressure to the second major surface of the backing layer to conform the perimeter of the wound dressing to a surface of skin surrounding the wound.

14. The method of claim 13, further comprising:
   (e) removing the dressing support layer from the wound dressing.

15. The method of claim 13, wherein the wound dressing and delivery system comprises at least two tabs having an included area of weakness.

* * * * *